United States Patent [19]

Hambleton et al.

[11] Patent Number: 5,384,423
[45] Date of Patent: Jan. 24, 1995

[54] 3-CYCLOALKYL-PROPANAMIDES

[75] Inventors: Philip T. Hambleton, Covingham; Charles J. R. Hedgecock, Wootton Bassett; David P. Kay, Purton; Elizabeth A. Kuo, Covingham; Wilfred R. Tully, Cirencester, all of Great Britain

[73] Assignee: Roussel-Uclaf, France

[21] Appl. No.: 51,178

[22] Filed: Apr. 22, 1993

Related U.S. Application Data

[62] Division of Ser. No. 785,087, Oct. 30, 1991, Pat. No. 5,240,960.

[30] Foreign Application Priority Data

Oct. 30, 1990 [GB] United Kingdom ............... 90-23535
Mar. 15, 1991 [GB] United Kingdom ............... 91-05516

[51] Int. Cl.$^6$ ............................................ C07C 255/40
[52] U.S. Cl. ...................................... 558/392; 549/439
[58] Field of Search ........................ 558/392; 549/439

[56] References Cited

U.S. PATENT DOCUMENTS 5,240,960 8/1993 Hambleton et al. ............... 558/392

FOREIGN PATENT DOCUMENTS

| 0326107 | 2/1989 | European Pat. Off. |
|---|---|---|
| 2057049 | 7/1971 | France ................... 558/392 |
| 2555789 | 7/1977 | Germany . |
| 48-5573 | 2/1973 | Japan ..................... 558/392 |
| 508803 | 7/1939 | United Kingdom ............... 558/392 |
| 930808 | 7/1963 | United Kingdom ............... 558/392 |

*Primary Examiner*—Joseph Paul Brust
*Attorney, Agent, or Firm*—Bierman and Muserlian

[57] ABSTRACT

A compound selected from the group consisting of all tautomeric forms of a cycloalkyl-propanamide of the formula

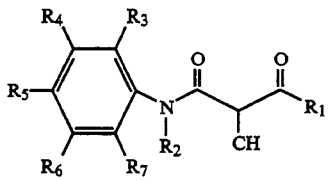

wherein $R_1$ is cycloalkyl of 3 to 6 carbon atoms, $R_2$ is hydrogen or alkyl of 1 to 3 carbon atoms, $R_3$, $R_4$, $R_5$, $R_6$ and $R_7$ are individually selected from the group consisting of hydrogen, halogen, —$NO_2$, azido, —CN, alkyl, alkoxy and alkylthio of 1 to 6 carbon atoms, —$(CH_2)_m$—$CF_3$, —O—$(CH_2)_m$—$CF_3$, —S—$(CH_2)_m$—$CF_3$, m is an integer from 0 to 3, —$CF_2$—Hal, —$OCF_2$—Hal,

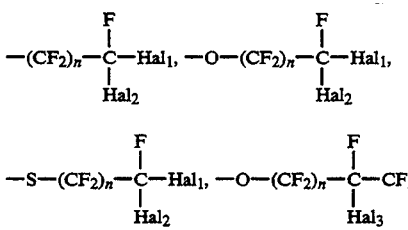

n is an integer from 1 to 3, Hal, $Hal_1$, and $Hal_2$ and $Hal_3$ are individually halogen, and —COR′, R′ is —OH or alkyl or alkoxy of 1 to 3 carbon atoms or $R_4$ and $R_5$ together are —O—$CH_2$—O— and their non-toxic, pharmaceutically acceptable basic salts having anti-inflammatory activity.

1 Claim, No Drawings

3-CYCLOALKYL-PROPANAMIDES

PRIOR APPLICATION

This application is a division of U.S. patent application Ser. No. 785,087 filed Oct. 30, 1991, now U.S. Pat. No. 5,240,960.

OBJECTS OF THE INVENTION

It is an object of the invention to provide the novel compounds of formula I and their non-toxic, pharmaceutically acceptable basic salts and a novel process and intermediates for their preparation.

It is another object of the invention to provide novel anti-inflammatory compositions and a novel method of treating inflammation in warm-blooded animals.

These and other objects and advantages of the invention will become obvious from the following detailed description.

THE INVENTION

The novel compounds of the invention are compounds selected from the group consisting of all tautomeric forms of a cycloalkylpropanamide of the formula

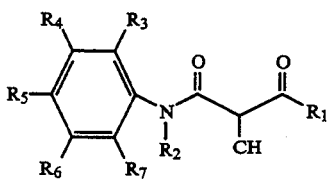

wherein $R_1$ is cycloalkyl of 3 to 6 carbon atoms, $R_2$ is hydrogen or alkyl of 1 to 3 carbon atoms, $R_3$, $R_4$, $R_5$, $R_6$ and $R_7$ are individually selected from the group consisting of hydrogen, halogen, $-NO_2$, azido, $-CN$, alkyl, alkoxy and alkylthio of 1 to 6 carbon atoms, $-(CH_2)_m-CF_3$, $-O-(CH_2)_m-CF_3$, $-S-(CH_2)_m-CF_3$, m is an integer from 0 to 3, $-CF_2-Hal$, $-OCF_2-Hal$,

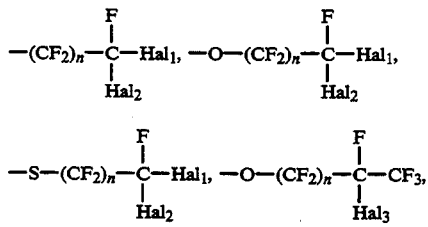

n is an integer from 1 to 3, Hal, $Hal_1$, $Hal_2$, and $Hal_3$ are individually halogen, and $-COR'$, $R'$ is $-OH$ or alkyl or alkoxy of 1 to 3 carbon atoms or $R_4$ and $R_5$ together are $-O-CH_2-O-$ and their non-toxic, pharmaceutically acceptable basic salts.

Examples of cycloalkyl of 3 to 6 carbon atoms are cyclopropyl, cyclobutyl, cyclopentyl and cyclohexyl. Examples of alkyl of 1 to 3 carbon atoms are methyl, ethyl, n-propyl and isopropyl. Examples of alkyl and alkoxy and alkylthio of 1 to 6 carbon atoms are methyl, ethyl, propyl, isopropyl, branched or linear butyl, pentyl and hexyl, methoxy, ethoxy, propoxy, isopropoxy, branched or linear butoxy, pentoxy and hexyloxy, methylthio, ethylthio, propylthio, isopropylthio and branched or linear butylthio, pentylthio and hexylthio.

Examples of halogen are fluorine, chlorine, bromine and iodine.

Examples of suitable bases for the non-toxic, pharmaceutically acceptable acid addition salts are inorganic bases such as salts of sodium, potassium, lithium, calcium magnesium and ammonium and organic bases such as methylamine, propylamine, trimethylamine, diethylamine, triethylamine, N,N-dimethyl-ethanolamine, tris(-hydroxymethyl)-aminomethane, ethanolamine, pyridine, picoline, dicyclohexylamine, morpholine, benzylamine, procaine, lysine, arginine, histidine and N-methyl-glucamine.

Among the preferred compounds of formula I are those wherein $R_3$, $R_4$, $R_5$, $R_6$ and $R_7$ are individually selected from the group consisting of hydrogen, fluorine, chlorine, bromine, iodine, methyl, ethyl, tert.-butyl, methoxy, methylthio, $-CF_3$, $-OCF_3$, $-SCF_3$, pentafluoroethyl, bromodifluoromethoxy, acetyl, hydroxycarbonyl, methoxycarbonyl, $-NO_2$, azido and $-CN$ or $R_4$ and $R_5$ together are $-O-CH_2-O-$, those wherein $R_2$ is hydrogen or methyl and their basic salts.

A more preferred group of compounds of formula I are those wherein $R_1$ is cyclopropyl, $R_2$ is hydrogen or methyl and $R_3$, $R_4$, $R_5$, $R_6$ and $R_7$ are individually selected from the group consisting of hydrogen, fluorine, chlorine, iodine, methyl, $-CF_3$ and nitro and their salts.

Specific preferred compounds of formula I are selected from the group consisting of 1-(4-nitrophenylcarbamoyl)-2-cyclopropyl-2-oxo-propionitrile, 1-(4-cyanophenylcarbamoyl)-2-cyclopropyl-2-oxo-propionitrile, 1-(4-chloro 3-methylphenylcarbamoyl)-2-cyclopropyl-2-oxo-propionitrile and 1-(3-methyl 4-trifluoromethyl-phenylcarbamoyl)-2-cyclobutyl-2-oxo-propionitrile and their non-toxic, 1-(4-cyano-3-methylphenylcarbamoyl)-2-cyclopropyl-2-oxo-propionitrile, pharmaceutically acceptable basic salts.

The novel process of the invention for the preparation of the compounds of formula I comprises reacting a compound of the formula

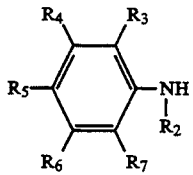

wherein $R_2$, $R_3$, $R_4$, $R_5$, $R_6$ and $R_7$ have the above definitions with a compound of the formula

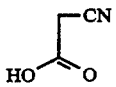

or an acid derivative thereof to form a compound of the formula

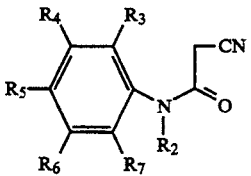

and then successively reacting the latter with sodium hydride in the optional presence of a catalyst such as imidazole, then with a compound of the formula R₁COHal    V wherein $R_1$ has the above definition and Hal is a halogen to obtain the compound of formula I which may be salified.

Preferably, the reaction of the compounds of formulae II and III is effected in the presence of diisopropylcarbodiimide or dichlorohexylcarbodiimide in an anhydrous organic solvent such as dichloromethane or tetrahydrofuran. The functional derivative of the acid of formula III is preferably cyanoacetyl chloride prepared in situ from phosphorus pentachloride and cyanoacetic acid.

The reaction of the compound of formula IV with sodium hydride is preferably effected in an anhydrous organic solvent such as tetrahydrofuran. The reaction with a compound of formula V is preferably effected in an anhydrous organic solvent such as dichloromethane.

The products of formula I have an acidic character and the addition salts may be effected by reacting approximately stoichiometric amounts of the compounds of formula I with a base with or without isolation of the compound of formula I.

The novel anti-inflammatory compositions of the invention are comprised of an anti-inflammatorily effective amount of at least one compound of formula I and its non-toxic, pharmaceutically acceptable basic salts and an inert pharmaceutical carrier. The compositions may be in the form of tablets, dragees, gelules, capsules, granules, suppositories or injectable solutions or suspensions.

Examples of suitable excipients are talc, arabic gum, lactose, starch, magnesium stearate, cocoa butter, aqueous or non-aqueous vehicles, fatty bodies of animal or vegetable origin, paraffinic derivatives, glycols, diverse wetting agents, dispersants or emulsifiers and preservatives.

The compositions have a remarkable anti-inflammatory activity and inhibit the inflammatory phenomena provoked by irritant agents and retard hypersensitive reactions caused by activation of immunitary cells by a specific antigen. The compositions may be used for the treatment of rhumatoid arthritis and chronic inflammatory conditions of immune or non-immune origin.

The novel method of treating inflammation in warm-blooded animals, including humans, comprises administering to warm-blooded animals an anti-inflammatorily effective amount of at least one compound of formula I or its non-toxic, pharmaceutically acceptable salts. The compounds may be administered orally, rectally or parenterally and the usual daily dose is 0.0013 to 2.66 mg/kg depending on the condition treated, the specific compound and the method of administration.

The novel intermediates of the invention are those of formula IV, especially those wherein $R_3$, $R_6$ and $R_7$ are hydrogen, $R_4$ is methyl and $R_2$ and $R_5$ have the above definition other than chlorine or methyl. They can be prepared by an analogous process of Nohara et al., J. Med. Chem., Vol. 28 (5) (1985), p. 559 to 566 by the following scheme:

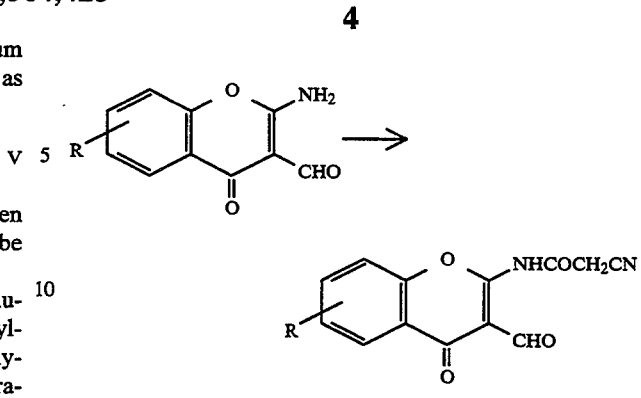

The compounds of formula II are generally known and are prepared by diazotation of the corresponding nitroanilines followed by reduction by known procedures. The nitroanilines can be prepared, for example, by the procedure of Suza et al., Synthetic Communications, Vol. 18, (1988) (16–17), p. 2161 to 2165.

Certain anilines of formula II are prepared in European patent No. 206,951 or by reduction of the corresponding nitrobenzenes by known methods. Certain nitrobenzenes are novel and are prepared as in the examples.

In the following examples, there are described several preferred embodiments to illustrate the invention. However, it is to be understood that the invention is not intended to be limited to the specific embodiments.

EXAMPLE 1

1-(4-trifluoromethylphenylcarbamoyl)-2-cyclopropyl-2-oxo-propionitrile

STEP A: 4-trifluoromethyl-cyanoacetanilide 16.4 ml of diisopropylcarbodiimide were added over 10 minutes while stirring without cooling to a solution of 8.6 g of cyanoacetic acid and 13.5 ml of 4-trifluoromethylaniline in 100 ml of tetrahydrofuran and the temperature during the addition ranged from 20° C. to 60° C. The mixture was stirred at room temperature for 16 hours and was filtered. The filtrate was evaporated to dryness and the residue was taken up in 100 ml of ethanol. The mixture was stirred at room temperature for one hour and was then filtered, washed with ethanol, then methylene chloride and hexane. The product was dried at 60° C. under reduced pressure for 3 hours to obtain 18.85 g of the expected product melting at 195° C. to 196° C.

STEP B: 1-(4-trifluoromethylphenylcarbamoyl)-2-cyclopropyl-2-oxo-propionitrile 0.88 g of sodium hydride were added to a suspension of 3 g of the product of Step A in 100 ml of tetrahydrofuran and the mixture was stirred at room temperature for 30 minutes. 1.30 ml of cyclopropanecarbonyl chloride were added over 10 minutes and the mixture was stirred at room temperature for 16 hours. After adding 1 ml of water, the mixture was stirred for 10 minutes and then was acidified with 2N hydrochloric acid. The mixture was extracted with ethyl acetate and the organic phase was dried and evaporated to dryness. The residue was heated in 15 ml of methylene chloride and diluted with ether to obtain 2.72 g of the expected product melting at 212° C. to 213° C.

Using the procedure of Example 1, the following products were prepared.

EXAMPLE 2

1-(3-chlorophenylcarbamoyl)-2-cyclopropyl 2-oxo-propionitrile.

EXAMPLE 3

1-(4-trifluoromethylphenylcarbamoyl) 2-cyclobutyl-2-oxo-propionitrile.

EXAMPLE 4

1-(4-trifluoromethylphenylcarbamoyl) 2-cyclopentyl-2-oxo-propionitrile.

EXAMPLE 5

1-(4-fluorophenylcarbamoyl) 2-cyclopropyl 2-oxo-propionitrile.

EXAMPLE 6

1-(4-chlorophenylcarbamoyl) 2-cyclopropyl 2-oxo-propionitrile.

EXAMPLE 7

1-(4-bromophenylcarbamoyl) 2-cyclopropyl 2-oxo-propionitrile.

EXAMPLE 8

1-(4-iodophenylcarbamoyl) 2-cyclopropyl 2-oxo-propionitrile.

STEP A: 4-iodocyanoacetanilide 14.41 g of cyanoacetic acid were added over 2 minutes with stirring to a suspension of 35.25 g of phosphorus pentachloride in 250 ml of methylene chloride while keeping the temperature at room temperature and after refluxing for 30 minutes, the mixture was stirred under a nitrogen atmosphere for 2 minutes. 24.75 g of 4-iodoaniline were added and the mixture was refluxed for 2 hours and then cooled. The mixture was poured into 300 ml of water and was stirred for one hour and filtered. The residue was taken up in an aqueous sodium bicarbonate solution and filtered. The solid residue was washed with water and ethanol and dried at 60° C. under reduced pressure to obtain 29.51 g of the expected product melting at 216° C. to 218° C.

STEP B: 1-(4-iodophenylcarbamoyl)-2-cyclopropyl-2-oxo-propionitrile

Using the procedure of step B of Example 1, the product of Step A was reacted to obtain the expected product.

Using the procedure of example 1, the following products were prepared.

EXAMPLE 9

1-(4-trifluoromethoxyphenylcarbamoyl) 2-cyclopropyl 2-oxo-propionitrile.

EXAMPLE 10

1-(4-nitrophenylcarbamoyl) 2-cyclopropyl 2-oxo-propionitrile.

EXAMPLE 11

1-(3,4-dichlorophenylcarbamoyl) 2 cyclopropyl 2-oxo-propionitrile.

EXAMPLE 12

1-(4-bromo-3-methylphenylcarbamoyl)-2-cyclopropyl-2-oxo-propionitrile

STEP A: 4-bromo-3-methyl-cyanoacetanilide

A mixture of 1.135 g of dicyclohexylcarbodiimide in 5 ml of methylene chloride was added with stirring at 40° C. over 2 minutes to a solution of 0.457 g of cyanoacetic acid and 1 g of 4-bromo-3-methylaniline in 30 ml of methylene chloride with the temperature being greater than 40° C. during the addition. After stirring at room temperature for one hour, the mixture was filtered to remove dicyclohexylurea and the filtrate was evaporated to dryness. The residue was chromatographed on silica and eluted with methylene chloride containing increasing amounts of ethyl acetate to obtain a 87% yield of the desired product.

STEP B: 1-(4-bromo-3-methylphenylcarbamoyl)-2-cyclopropyl-2-oxo-propionitrile

A catalytic amount of imidazole was added to a stirred solution of 300 mg of the product of Step A in 12 ml of tetrahydrofuran under nitrogen and after the addition of 626 mg of sodium hydride, the mixture was stirred at room temperature for 15 minutes. 124 mg of cyclopropanecarbonyl chloride were added over 3 minutes and the mixture was stirred at room temperature for 3 hours and then was poured into ice water. The mixture was acidified to a pH of 2 by 1M hydrochloric acid and after stirring for one minute, the mixture was filtered. The precipitate was washed with water, then ether to obtain a 88.3% yield of the desired product.

EXAMPLE 13

1-(3,4-methylenedioxy-phenylcarbamoyl)-2-cyclopropyl-2-oxo-propionitrile

STEP A: 3,4-methylenedioxy-cyanoacetanilide 279 mg of cyanoacetic acid were added with stirring over one minute to a suspension of 685 mg of phosphorus pentachloride in 10 ml of methylene chloride while maintaining room temperature and the mixture was refluxed for 30 minutes. After stirring under nitrogen for 2 minutes, 300 mg of 3,4-methylene-dioxy-aniline were added to the mixture which was then refluxed for 10 minutes and cooled to room temperature. The mixture was poured into 10 ml of water and was stirred for 30 minutes and filtered. The product was washed with water, then ether and ethyl acetate to obtain 330 mg of the desired product.

STEP B: 1-(3,4-methylenedioxy-phenylcarbamoyl)-2-cyclopropyl-2-oxo-propionitrile Using the procedure of Step B of Example 1, the product of Step A was reacted to obtain the desired product.

Using the said procedure, the following compounds were prepared.

EXAMPLE 14

2-cyano-3-cyclopropyl-3-oxo-N-methyl-N-(4-chlorophenyl)-propionamide.

EXAMPLE 15

1-(4-chloro-2-methylphenylcarbamoyl)-2-cyclopropyl-2-oxo-propionitrile.

EXAMPLE 16

1-(3,4-difluorophenylcarbamoyl)-2-cyclopropyl-2-oxo-propionitrile.

EXAMPLE 17

1-(4-methoxyphenylcarbamoyl)-2-cyclopropyl-2-oxo-propionitrile.

EXAMPLE 18
1-(4-cyano-phenylcarbamoyl)-2-cyclopropyl-2-oxo-propionitrile.

EXAMPLE 19
1-(3,5-dichlorophenylcarbamoyl)-2-cyclopropyl-2-oxo-propionitrile.

EXAMPLE 20
1-(4-chloro-3-methylphenylcarbamoyl)-2-cyclopropyl-2-oxo-propionitrile.

EXAMPLE 21
1-(3-trifluoromethylphenylcarbamoyl)-2-cyclopropyl-2-oxo-propionitrile.

EXAMPLE 22
1-(4-methylphenylcarbamoyl)-2-cyclopropyl-2-oxo-propionitrile.

EXAMPLE 23
1-(4-chloro-3-trifluoromethylphenylcarbamoyl)-2-cyclopropyl-2-oxo-propionitrile.

EXAMPLE 24
1-(phenylcarbamoyl)-2-cyclopropyl-2-oxo-propionitrile.

EXAMPLE 25
1-(3-methyl-4-trifluoromethylphenylcarbamoyl)-2-cyclopropyl-2-oxo-propionitrile.

EXAMPLE 26
1-(4-iodo-3-methylphenylcarbamoyl)-2-cyclopropyl-2-oxo-propionitrile.

EXAMPLE 27
1-(4-fluoro-3-methylphenylcarbamoyl)-2-cyclopropyl-2-oxo-propionitrile.

EXAMPLE 28
1-(4-cyano-3-methylphenylcarbamoyl)-2-cyclopropyl-2-oxo-propionitrile.

EXAMPLE 29
1-(4-(2,2,2-trifluoroethoxy)-phenylcarbamoyl)-2-cyclopropyl-2-oxo-propionitrile.

EXAMPLE 30
1-(3-methyl-4-nitrophenylcarbamoyl)-2-cyclopropyl-2-oxo-propionitrile.

EXAMPLE 31
1-(4-t-butylphenylcarbamoyl)-2-cyclopropyl-2-oxo-propionitrile.

EXAMPLE 32
1-(3-methylphenylcarbamoyl)-2-cyclopropyl-2-oxo-propionitrile.

EXAMPLE 33
1-(4-trifluoromethylthiophenylcarbamoyl)-2-cyclopropyl-2-oxo-propionitrile.

EXAMPLE 34
1-(4-methoxycarbonylphenylcarbamoyl)-2-cyclopropyl-2-oxo-propionitrile.

EXAMPLE 35
1-(4-acetylphenylcarbamoyl)-2-cyclopropyl-2-oxo-propionitrile.

EXAMPLE 36
1-(3,4-dimethoxyphenylcarbamoyl)-2-cyclopropyl-2-oxo-propionitrile.

EXAMPLE 37
1-(3-chloro-4-methylphenylcarbamoyl)-2-cyclopropyl-2-oxo-propionitrile.

EXAMPLE 38
1-(4-methylthiophenylcarbamoyl)-2-cyclopropyl-2-oxo-propionitrile.

EXAMPLE 39
1-(3-ethyl-4-nitrophenylcarbamoyl)-2-cyclopropyl-2-oxo-propionitrile.

EXAMPLE 40
2-cyano-3-cyclopropyl-3-oxo-N-methyl-N-(3-methyl-4-trifluoromethylphenyl)-propionamide.

EXAMPLE 41
1-(4-bromodifluoromethoxy-3-methylphenylcarbamoyl)-2-cyclopropyl-2-oxo-propionitrile.

EXAMPLE 42
2-cyano-3-cyclopropyl-3-oxo-N-methyl-N-(4-cyanophenyl)-propionamide.

EXAMPLE 43
2-cyano-3-cyclopropyl-3-oxo-N-methyl-N-(4-nitrophenyl)propionamide.

EXAMPLE 44
1-(3-methyl-4-trifluoromethoxyphenylcarbamoyl)-2-cyclopropyl-2-oxo-propionitrile.

EXAMPLE 45
1-(3-methyl-4-pentafluoroethylphenylcarbamoyl)-2-cyclopropyl-2-oxo-propionitrile.

EXAMPLE 46
2-cyano-3-cyclopropyl-3-oxo-N-methyl-N-(4-bromo-3-methylphenyl)-propionamide.

EXAMPLE 47
1-(4-chloro-3-ethylphenylcarbamoyl)-2-cyclopropyl-2-oxo-propionitrile.

EXAMPLE 48
1-(4-carboxyphenylcarbamoyl)-2-cyclopropyl-2-oxo-propionitrile.

EXAMPLE 49
1-(3-methyl-4-trifluoromethylthiophenylcarbamoyl)-2-cyclopropyl-2-oxo-propionitrile.

Preparation of
1-(bromodifluoromethoxy)-2-methyl-4-amino-benzene
for Example 41

6 g of 2-methyl-4-nitro-phenol were added to a solution of 0.92 g of sodium in 30 ml of ethanol and after evaporation under reduced pressure, the residue was added to benzene. The sodium salt was added to a mixture of 24 ml of dimethylformamide, 30 ml of dibromodifluoromethane and a small amount of ethanethiol as catalyst and after heating at 70° C. for 10 hours, the mixture was poured into ice and was extracted with ethyl acetate. The organic phase was washed with 0.5M aqueous sodium hydroxide, then with water, dried and evaporated to dryness under reduced pressure. The residue was chromatographed over silica (eluant—ethyl acetate—hexane 4-96) to obtain 0.20 g of 1-(bromodifluoromethoxy)-2-methyl-4-amino-benzene which was hydrogenated in the presence of palladized active characoal to obtain the desired product.

Preparation of
2-methyl-4-amino-1-trifluoromethoxy-benzene for Example 44

A mixture of 0.3 g of 1-(bromodifluoromethoxy)-2-methyl-4-nitro-benzene, 0.120 g of antimony trifluoride and 0.02 g of antimony pentachloride as catalyst was heated at 175° C. in a sealed flask for 4 hours and was then diluted with ether. The mixture was washed with water, dried and evaporated to dryness under reduced pressure to obtain 0.13 g of 1-trifluoromethoxy-2-methyl-4-nitro-benzene which was hydrogenated in the presence of palladized active charcoal to obtain the desired product.

Preparation of
1-pentafluoroethyl-2-methyl-4-amino-benzene for Example 45

A mixture of 2.36 g of 1-iodo-2-methyl-4-nitro-benzene and 2.2 g of powdered copper (Org. Synthesis Coll., Vol. II (1948), page 445 washed with water, acetone and dried under reduced pressure) in 10 ml of dimethylformamide under nitrogen in a sealed vessel was cooled to −60° C. and 11.5 g of pentafluoroethyl iodide were added. The mixture was stirred at 160° C. at a pressure of 3.5 bars for 16 hours and then cooled in ice and returned to room temperature. The mixture was poured into ice and was extracted with ethyl acetate. The organic phase was washed with water, dried and evaporated to dryness under reduced pressure. The residue was chromatographed over silica (eluant—pentane containing 2 to 3% of dichloromethane) to obtain 1.5 g of 1-pentafluoroethyl-2-methyl-4-nitro-benzene which was hydrogenated in the presence of palladized active carbon to obtain the desired product.

The spectrometric analysis, microanalysis results, yields and melting points of the above compounds are reported in the following Tables.

TABLE I

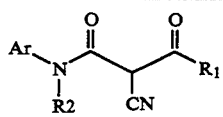

| Example | Ar | R2 | R1 | Yield | MP °C. | IR Spectrum cm − 1 |
|---|---|---|---|---|---|---|
| 1 | CF₃—C₆H₄— | H | cyclopropyl | 70% | 212–3 | 3280(NH), 2202(CN), 1620, 1602, 1575, 1540, 1410, 1320, 1100 |
| 2 | 2-Cl—C₆H₄— | H | cyclopropyl | 44% | 137–9 | 3280(NH), 2203(CN), 1620, 1600, 1568, 1535, 1477, 1408, 1395, 1345, 1300, 1253, 1221 |
| 3 | CF₃—C₆H₄— | H | cyclobutyl | 66% | 177–8 | 3260(NH), 2200(CN), 1621, 1601, 1574, 1540, 1317, 1150, 1110, 1056, 832 |
| 4 | CF₃—C₆H₄— | H | cyclopentyl | 73% | 177–80 | 3280(NH), 2000(CN), 1625, 1600, 1574, 1540, 1320, 1118, 1108, 1061, 832 |
| 5 | F—C₆H₄— | H | cyclopropyl | 74% | 187–8 | 3310(NH), 2200(CN), 1610, 1580, 1540, 1526, 1502, 1403, 1200, 885, 823 |
| 6 | Cl—C₆H₄— | H | cyclopropyl | 89% | 189–91 | 3280(NH), 2200(CN), 1620, 1597, 1569, 1539, 1525, 1482, 1381, 1392, 1302, 1230, 885, 820 |

TABLE I-continued $$\underset{R_2}{Ar-N}-\overset{O}{\underset{CN}{C}}-CH-\overset{O}{C}-R_1$$

| # | Ar | R2 | R1 | Yield | mp | IR |
|---|---|---|---|---|---|---|
| 7 | 4-Br-C6H4- | H | cyclopropyl | 81% | 190-2 | 3275(NH), 2200(CN), 1620, 1590, 1565, 1540, 1520, 1479, 1383, 1343, 1302, 1229, 886 |
| 8 | 4-I-C6H4- | H | cyclopropyl | 81% | 182-4 | 3275(NH), 2204, 1615, 1595, 1575, 1540, 1478, 1404, 1387, 1348, 886, 811 |
| 9 | 4-CF3O-C6H4- | H | cyclopropyl | 83% | 173-5 | 3285(NH), 2206(CN), 1627, 1608, 1579, 1540, 1502, 1417, 1381, 1270, 1233, 1210, 1153, 891, 842 |
| 10 | 4-NO2-C6H4- | H | cyclopropyl | 94% | 235-6 | 3290(NH), 2205(CN), 1612, 1555, 1496, 1418, 1338, 1310, 1270, 1242, 1190, 1180, 1114, 1084, 1062, 890, 864 |
| 11 | 3,4-Cl2-C6H3- | H | cyclopropyl | 60% | 196 | 3305(NH), 2205(CN), 1630, 1602, 1570, 1525, 1480, 1450, 1405, 1342, 1302, 1270, 1250, 1225 |
| 12 | 2-Me-4-Br-C6H3- (actually 4-Br-2-Me) | H | cyclopropyl | 88% | 158 | 3280(NH), 2180(CN), 1600, 1580, 1510, 1470, 1435, 1395, 1330, 1290, 1270, 1245, 1220 |
| 13 | 3,4-(OEt,O)-C6H3- | H | cyclopropyl | 32% | 152 | 3305(NH), 3075, 2885, 2195(CN), 1630, 1580, 1540, 1480, 1425, 1280, 1255, 1235, 1200 |
| 14 | 4-Cl-C6H4- | CH3 | cyclopropyl | 45% | 135-7 | 2180(CN), 1591, 1581, 1562, 1550, 1467, 1425, 1389, 1071, 1042, 1017, 877 |
| 15 | 4-Cl-2-Me-C6H3- | H | cyclopropyl | 45% | 167 | 3290(NH), 3020, 2205(CN), 1890, 1400, 1350, 1295, 1185, 1120, 1080, 1060, 1025, 985, 940, 885, 850, 805, 770, 750 |
| 16 | 3,4-F2-C6H3- | H | cyclopropyl | 50% | 177 | 3301(NH), 2210(CN), 1602, 1545, 1510, 1440, 1345, 1278, 1240 1208, 1150, 1110, 1080, 1065, 1025, 965, 890, 805, 775, 665 |
| 17 | 4-MeO-C6H4- | H | cyclopropyl | | | |

TABLE I-continued
Ar\\N(R2)—C(=O)—CH(CN)—C(=O)—R1
| # | Ar | R2 | R1 | Yield | mp | IR |
|---|----|----|----|-------|-----|-----|
| 18 | 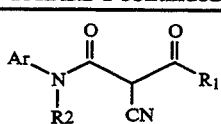 (4-NC-C6H4) | H | 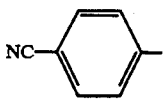 (cyclopropyl) | 53% | 236, 5 | 3350(NH), 2180(CN), 1890(CN) |
| 19 |  (2,4-Cl2-C6H3) | H | 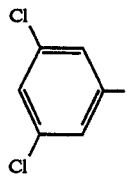 | 72% | 159, 5 | |
| 20 |  (2-Me-4-Cl-C6H3) | H | 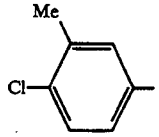 | | | |
| 21 |  (3-CF3-C6H4) | H | 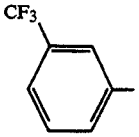 | — | | 3710(NH), 2035(CN), 1545, 1520, 1495, 1460, 1400, 1310, 1260, 1240, 1170, 1130, 1060, 1025 |
| 22 |  (4-CH3-C6H4) | H | 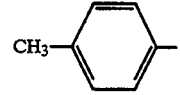 | — | | |
| 23 |  (2-Cl-5-CF3-C6H3) | H | 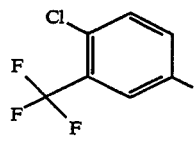 | | 207 | 3280(NH), 2220(CN), 1620, 1520, 1470, 1400, 1340, 1305, 1260, 1220, 1080, 1020, 975, 910, 890, 820, 755, 685, 655, 620 |
| 24 |  (C6H5) | H | 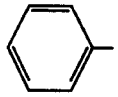 | | 117 | 3290(NH), 2220(CN), 1600, 1450, 1415, 1350, 1320, 1265, 1245, 1195, 1180, 1090, 1065, 1030, 990, 920, 895, 805, 770, 755, 695 |
| 25 |  (2-CF3-4-Me-C6H3) | H | 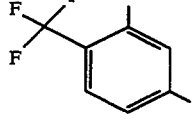 | | 186–8 | 3395(NH), 2204(CN), 1630, 1600, 1580, 1545, 1409, 1346, 1310, 1156, 1110, 1097, 1037, 1027, 888, 877, 831 |
| 26 |  (2-I-4-Me-C6H3) | H | 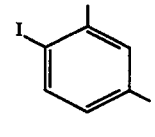 | | 163–5 | 3284(NH), 2000(CN), 1623, 1599, 1565, 1525, 1469, 1400, 1371, 1338, 1301, 1250, 1238, 882 |
| 27 |  (2-F-4-Me-C6H3) | H | 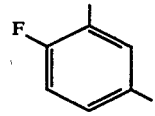 | | 140–2 | 3280(NH), 2002(CN), 1620, 1573, 1560, 1540, 1491, 1341, 1204, 886 |

TABLE I-continued
Ar—N(R2)—C(=O)—CH(CN)—C(=O)—R1
| | Ar | R2 | R1 | mp (°C) | IR (cm⁻¹) |
|---|---|---|---|---|---|
| 28 | 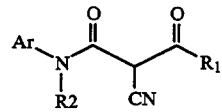 | H | 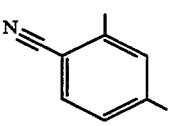 | 300 | 3280(NH), 2195s(CN), 2145w(CN), 1630, 1588, 1551, 1500, 1410, 1332, 1309, 1254, 1230, 877, 821 |
| 29 |  | H | 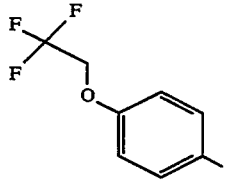 | — | 3380(NH), 2002(CN), 1621, 1602, 1578, 1551, 1540, 1502, 1477, 1350, 1280, 1220, 1150, 1071, 889 |
| 30 |  | H | 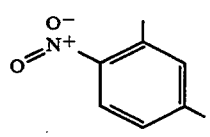 | 223–6 | 3300, 3120, 2930, 2220, 1630, 1570, 1550, 1500, 1450, 1420, 1380, 1350, 1290, 1270, 1240, 1090, 1070, 1040 |
| 31 |  | H | 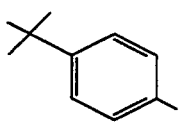 | 141–3 | 3260, 2970, 2210, 1910, 1590, 1410, 1350, 1300, 1270, 1195, 1120, 1095, 1070, 1020, 995, 950, 905, 870, 840, 825, 805, 770, 730, 675 |
| 32 |  | H | 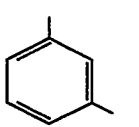 | 102–4 | |
| 33 |  | H | 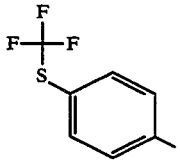 | 175–6 | 3280(NH), 2212(CN), 1621, 1597, 1570, 1527, 1490, 1346, 1310, 1130(s), 1110, 1090, 892, 829 |
| 34 |  | H | 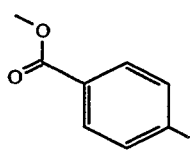 | 188–9 | 3360(m), 3322(m), 2200(m), 1710(s), 1576(s), 1524(s), 1429(m), 1409(s), 1348(m), 1318(m), 1275(s), 1241(m), 1189(m), 1107(m), 1081(m), 985(m), 894(m), 763(m) |
| 35 |  | H | 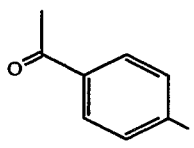 | 158–60 | 3300, 2920, 2840, 2200, 1660, 1580, 1510, 1450, 1345, 1305, 1260, 1240, 1175, 1065, 1035, 980, 915, 890, 870, 835, 820, 805, 760 |
| 36 |  | H | 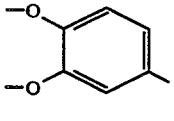 | 162–4 | 3290, 2905, 2820, 2210, 1575, 1550, 1505, 1460, 1435, 1410, 1395, 1355, 1290, 1270, 1250, 1225, 1160, 1130, 1080, 1020, 890, 840, 805, 760, 710, 690, 680 |
| 37 |  | H | 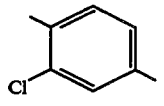 | 122–4 | 3290, 2200, 1565, 1520, 1490, 1440, 1405, 1380, 1340, 1305, 1250, 1230, 1180, 1080, 1040, 995, 885, 865, 810, 680 |

TABLE I-continued

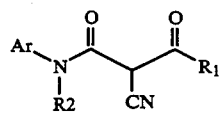

| # | Ar | R2 | R1 | mp (°C) | IR |
|---|---|---|---|---|---|
| 38 | 4-(methylthio)phenyl | H | cyclopropyl | 141-2 | 3280, 2205, 1570, 1525, 1485, 1395, 1360, 1305, 1280, 1235, 1080, 1060, 970, 890, 815, 760, 665 |
| 39 | 2-ethyl-4-methyl-nitrobenzene | H | cyclopropyl | 179-81 | 3290(s), 2210(s), 1610(m), 1570(s), 1525(s), 1410(s), 1330(s), 1240(s), 880(m) |
| 40 | 2-(trifluoromethyl)-4-methylphenyl | CH3 | cyclopropyl | 108, 5-110 | 2220, 1560, 1460, 1380, 1320, 1170, 1130, 1050 |
| 41 | 2-(bromodifluoromethoxy)-4-methylphenyl | H | cyclopropyl | 165-7 | 3280(NH), 2198(CN), 1620, 1600, 1575, 1552, 1540, 1481, 1400, 1253, 1200, 1185, 1131, 990, 886 |
| 42 | 4-cyanophenyl | CH3 | cyclopropyl | 141-3 | 2260, 2230, 1570, 1520, 1470, 1390, 1210, 1110, 1080, 1050, 1030 |
| 43 | 4-nitrophenyl | CH3 | cyclopropyl | 141, 5-142, 5 | 2220, 1607, 1530, 1510, 1480, 1450, 1200, 1100, 1040, 1020 |
| 44 | 2-(trifluoromethoxy)-4-methylphenyl | H | cyclopropyl | 148-50 | 3285(NH), 2006(CN), 1627, 1580, 1560, 1543, 1421, 1280, 1260, 1242, 1200, 1141, 889 |
| 45 | 2-(pentafluoroethyl)-4-methylphenyl | H | cyclopropyl | 135-7 | 3275(NH), 2204(CN), 1610, 1590, 1560, 1525, 1410, 1340, 1307, 1285, 1254, 1185, 1132, 1112, 1066, 962, 881 |
| 46 | 2-bromo-4-methylphenyl | CH3 | cyclopropyl | 138-9 | 2220, 1570, 1490, 1400, 1240, 1210, 1110, 1050 |

TABLE I-continued

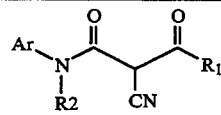

| | | | | | |
|---|---|---|---|---|---|
| 47 | [2-chloro-5-methyl ethylbenzene structure] | H | [cyclopropyl] | 169–70 | 3340, 2240, 1635, 1540, 1495, 1320, 900 |
| 48 | [4-methylbenzoic acid structure] | H | [cyclopropyl] | | |

| Example | NMR Spectrum | Formula MW | Calculated Found | | | |
|---|---|---|---|---|---|---|
| | | | C % | H% | N % | X % |
| 1 | CDCl3 - 15, 64(1H, s); 7, 77(1H, s); 7, 64(4H, s); 2, 16(1H, m); 1, 37(2H, m); 1, 18(2H, m) | C14H11O2N2F3 282, 26 | 56, 76 | 3, 74 | 9, 46 | 19, 25 |
| 2 | CDCl3 - 1570(1H, s); 7, 65(1H, s); 7, 63(1H, s); 7, 25(3H, m); 2, 16(1H, m); 1, 34(2H, m); 1, 18(2H, m) | C13H11N2O2Cl 262, 69 | 59, 44 | 4, 22 | 10, 66 | 13, 49 |
| 3 | CDCl3 - 15, 61(1H, s); 7, 76(1H, s); 7, 64(4H, s); 3, 66(1H, m); 2, 24(6H, m) | C15H13N2O2F3 310, 28 | 58, 07 58, 03 | 4, 22 4, 28 | 9, 02 9, 02 | 18, 37 18, 43 |
| 4 | CDCl3 - 15, 51(1H, s); 7, 72(1H, s); 7, 64(4H, s); 3, 22(1H, m); 1, 85(8H, m) | C16H15N2O3F3 324, 31 | 59, 26 59, 17 | 4, 66 4, 69 | 8, 64 8, 63 | 17, 58 17, 63 |
| 5 | CDCl3 - 15, 83(1H, s); 7, 61(1H, s); 7, 42(2H, m); 7, 06(2H, m); 2, 15(1H, m); 1, 32(2H, m); 1, 16(2H, m) | C13H11N2O2F 246, 24 | 63, 41 — | 4, 50 — | 11, 38 — | 13, 00 — |
| 6 | CDCl3 - 15, 77(1H, s); 7, 63(1H, s); 7, 44(2H, d); 7, 33(2H, d); 2, 14(1H, m); 1, 31(2H, m); 1, 16(2H, m) | C13H11N2O2Cl 262, 69 | 59, 44 59, 35 | 4, 22 4, 30 | 10, 66 10, 67 | 13, 49 13, 51 |
| 7 | CDCl3 - 15, 76(1H, s); 7, 62(1H, s); 7, 48(2H, d); 7, 38(2H, d); 2, 14(1H, m); 1, 32(2H, m); 1, 25(2H, m) | C13H11N2O2Br 307, 15 | 50, 84 — | 3, 61 — | 9, 12 — | 26, 02 — |
| 8 | CDCl3 - 15, 71(1H, s); 7, 67(2H, s); 7, 53(1H, s); 7, 26(2H, m); 2, 14(1H, m); 1, 34(2H, m); 1, 16(2H, m) | C13H11N2O2I 354, 14 | 44, 09 — | 3, 13 — | 7, 91 — | 35, 83 — |
| 9 | CDCl3 - 15, 76(1H, s); 7, 73(1H, s); 7, 53(2H, d); 7, 22(2H, d); 2, 15(1H, m); 1, 31(2H, m); 1, 18(2H, m) | C14H11N2O3F3 312, 26 | 53, 85 — | 3, 55 — | 8, 97 — | 18, 25 — |
| 10 | DMSO - 12, 27(1H, s); 8, 19(2H, d); 7, 79(2H, d); 2, 20(1H, m); 0, 89(4H, m) | C13H11N3O4 273, 25 | 57, 14, — | 4, 07 — | 15, 38 — | |
| 11 | DMSO - 11, 536(1H, s); 8, 04(1H, m); 7, 52(1H, m); 7, 45(1H, m); 2, 19(1H, m); 0, 95(4H, m) | C13H10Cl2N2O2 297, 14 | 52, 55 52, 37 | 3, 39 3, 45 | 9, 43 9, 37 | 23, 86 — |
| 12 | DMSO - 10, 97 (1H, s); 7, 54(2H, m); 7, 39(1H, m); 2, 34(3H, s); 2, 19(1H, m); 1, 03(4H, m) | C14H13N2O2Br 321, 164 | 52, 35 52, 37 | 4, 08 4, 10 | 8, 72 8, 65 | 24, 88 24, 10 |
| 13 | CDCl3 - 15, 89(1H, s); 7, 44(1H, s); 7, 10(1H, m); 6, 78(2H, m); 5, 99(2H, s); 2, 10(1H, m); 1, 26(4H, m) | C14H12N2O4 272, 266 | 61, 76 61, 65 | 4, 44 4, 47 | 10, 29 10, 18 | — |
| 14 | CDCl3 - 17, 09(1H, s); 7, 44(2H, d); 7, 23(2H, d); 3, 34(3H, m); 2, 13(1H, m); 1, 24(2H, m); 1, 03(2H, m) | C14H13N2O2Cl 276, 72 | 60, 77 | 4, 73 | 10, 12 | 12, 82 |
| 15 | DMSO - 10, 807(1H, s); 7, 72(1H, m); 7, 35(1H, m); 7, 27(1H, m); 2, 22(3H, m); 2, 19(1H, m); 1, 02(4H, m) | C14H13N2O2Cl 276, 714 | 60, 76 60, 69 | 4, 74 4, 77 | 10, 13 10, 10 | 12, 81 12, 82 |
| 16 | DMSO - 11, 20(1H, s); 7, 80(1H, m); 7, 37(2H, m); 2, 19(1H, m); 1, 01(4H, m) | C13H10N2O2F2 264, 23 | 59, 09 | 3, 81 | 10, 60 | 14, 38 |
| 17 | | | | | | |
| 18 | DMSO - 11, 89(1H, s); 7, 74(4H, m); 2, 2(1H, m); 0, 9(4H, m) | C14H11N3O2 253, 932 | 66, 21 — | 4, 37 — | 16, 55 — | — |
| 19 | DMSO - 11, 89(1H, s); 7, 66(2H, m); 7, 18(1H, s); 2, 19(1H, m); 0, 88(4H, m) | C13H10N2Cl2 297, 132 | 52, 55 — | 3, 39 — | 9, 43 — | 23, 86 — |
| 20 | | C14H14N2O2 242, 2 | 69, 4 — | 5, 825 — | 11, 57 — | 13, 21 — |
| 21 | DMSO - 11, 57(1H, s); 8, 12(1H, m); 7, 68(1H, m); 7, 36(1H, m); 2, 20(1H, m); 0, 91(4H, m) | C14H11N2O2F3 296, 25 | 56, 76 — | 3, 74 — | 9, 46 — | 19, 25 — |
| 22 | | C14H14N2O2 242, 26 | 69, 4 | 5, 82 | 11, 86 | — |
| 23 | DMSO - 11, 49(1H, s); 8, 23(1H, m); 7, 81(1H, m); 7, 67(1H, m); 2, 22(1H, m); 1, 07(4H, m) | C14H10ClF3N2O2 330, 70 | 50, 85 50, 71 | 3, 05 3, 16 | 8, 47 8, 39 | 10, 72 10, 73 |
| | | | | | Calculé F % 17, 23 | |
| 24 | DMSO - 10, 68(1H, s); 7, 53(2H, m); 7, 36(2H, m); 7, 17(1H, m); 2, 20(1H, m); 1, 09(4H, m) | C13H12N2O2 228, 25 | 68, 41 68, 40 | 5, 30 5, 37 | 12, 27 12, 32 | — |
| 25 | CDCl3 - 15 ,63(1H, s); 7, 59(2H, d); 7, 43(2H, d); 2, 49(3H, s); 2, 15(1H, m); 1, 35(2H, m); 1, 19(2H, m) | C15H13F3N2O2 310, 28 | 58, 07 58, 00 | 4, 22 4, 30 | 9, 03 9, 04 | 18, 37 18, 27 |
| 26 | CDCl3 - 15, 73(1H, s); 7, 77(1H, d); 7, 45(1H, s); 7, 37(1H, d); 7, 06(1H, dd); 2, 43(3H, s); 2, 14(1H, m); 1, 34(2H, m); 1, 17(2H, m) | C14H13IN2O2 368, 18 | 45, 67 — | 3, 56 — | 7, 61 — | 34, 47 — |
| 27 | CDCl3 - 15, 85(1H, s); 7, 49(1H, s); 7, 24(2H, m); | C14H13FN2O2 | 64, 61 | 5, 03 | 10, 76 | 7, 30 |

TABLE I-continued

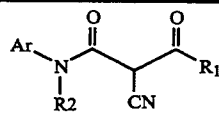

| # | NMR | Formula / MW | C | H | N | Other |
|---|---|---|---|---|---|---|
| | 7, 00(1H, t); 2, 28(3H, s); 1, 33(2H, m); 1, 16(2H, m) | 260, 27 | — | — | — | — |
| 28 | DMSO - 12, 01(1H, s); 7, 63(3H, m); 2, 45(3H, s); 2, 21(1H, m); 0, 88(4H, m) | $C_{15}H_{13}N_3O_2$ 267, 29 | 67, 41 — | 4, 90 — | 15, 72 — | — — |
| 29 | CDCl3 - 15, 87(1H, s); 7, 52(2H, m); 7, 42(2H, m); 7, 95(2H, m); 4, 34(2H, q); 2, 15(1H, m); 1, 33(2H, m); 1 ,16(2H, m) | $C_{15}H_{13}F_3N_2O_3$ 326, 28 | 55, 22 — | 4, 02 — | 8, 59 — | 17, 47 — |
| 30 | DMSO - 11, 65(1H, s); 8, 02(1H, d); 7, 65(1H, m); 2, 53(3H, s); 2, 17(1H, m); 0, 95(4H, m) | $C_{14}H_{13}N_3O_4$ 287, 28 | 58, 53 — | 4, 56 — | 14, 63 — | — — |
| 31 | DMSO - 10, 65(1H, s); 7, 37(2H, m); 7, 26(1H, m); 6, 97(1H, m); 2, 32(3H, s); 2, 19(1H, m); 1, 08(4H, m) | $C_{17}H_{20}N_2O_2$ 284, 36 | 71, 81 — | 7, 09 — | 9, 85 — | — — |
| 32 | | $C_{14}H_{14}N_2O_2$ 242, 28 | 69, 41 — | 5, 82 — | 11, 56 — | — — |
| 33 | CDCl3 - 15, 62(1H, s); 7, 66(2H, d); 7, 58(2H, d); 2, 16(1H, m); 1, 35(2H, m); 1, 19(2H, m); 192, 51; 167, 94; 138, 71; 137, 41; 129, 39(q, J=309Hz); 121, 41; 120, 40; 15, 91; 11, 19 | $C_{14}H_{11}F_3N_2O_2S$ 328, 32 | 51, 22 — Calculé S % 9, 77 | 3, 38 — | 8, 53 — | 17, 36 — |
| 34 | CDCl3 - 1, 14-1, 25(2H, m); 1, 31-1, 41(2H, m); 2, 10-2, 20(1H, m); 3, 92(3H, s); 7, 59(2H, d, J=8, 6) Hz); 7, 66(1H, s); 8, 05(2H, d, J=8, 4); 15, 63(1H, s) | $C_{15}H_{14}N_2O_4$ 286, 29 | 62, 93 — | 4, 93 — | 9, 78 — | — — |
| 35 | DMSO - 11, 86(1H, s); 7, 92(2H, m); 7, 69(2H, m); 2, 52(3H, m); 2, 17(1H, m); 0, 88(4H, m) | $C_{15}H_{14}N_2O_3$ 270, 29 | 66, 66 — | 5, 22 — | 10, 36 — | — — |
| 36 | DMSO - 10, 44(1H, s); 7, 22(1H, m); 7, 11(1H, m); 6, 95(1H, m); 3, 76(6H, s); 2, 19(1H, m); 1, 07(4H, m) | $C_{15}H_{16}N_2O_4$ 288, 31 | 62, 49 — | 5, 59 — | 9, 70 — | — — |
| 37 | DMSO - 11, 21(1H, s); 7, 81(1H, s); 7, 28(2H, s); 2, 30(3H, s); 2, 19(1H, m); 0, 98(1H, m) | $C_{14}H_{13}ClN_2O_2$ 276, 72 | 60, 77 — | 4, 74 — | 10, 12 — | 12, 81 — |
| 38 | DMSO - 10, 66(1H, s); 7, 52(2H, m); 7, 27(2H, m); 2, 52(3H, s); 2, 20(1H, m); 1, 06(4H, m) | $C_{14}H_{14}N_2O_2S$ 274, 34 | 61, 29 — | 5, 14 — | 10, 21 — | 11, 69 — |
| 39 | DMSO - 11, 82(1H, s-NH); 8, 00(1H, d, J=9Hz, H-5); 7, 71(1H, dd, J-32 9Hz, J=2Hz, H-6); 7, 63(1H, d, J=2Hz, H-2); 2, 91(2H, q, J=7, 4Hz, 3THYL-CH2); 2, 28-2, 16(1H, m, cyclopropyl 1-H); 1, 24(3H, t, J=7, 4Hz, —CH3); 0, 97-0, 87(4H, m, cyclopropyl) | $C_{15}H_{15}N_3O_4$ 301, 30 | 59, 80 — | 5, 02 — | 13, 95 — | — — |
| 40 | CDCl3 - 16, 99(1H, s); 7, 69(1H, d); 7, 23(2H, d); 3, 37(3H, s); 2, 53(3H, s); 2, 14(1H, m); 1, 15(4H, m) | $C_{16}H_{15}F_3N_2O_2$ 324, 31 | 59, 26 — | 4, 66 — | 8, 64 — | 17, 57 — |
| 41 | CDCl3 - 15, 72(1H, s); 7, 54(1H, s); 7, 33(3H, m); 2, 32(3H, s); 2, 15(1H, m); 1, 33(2H, m); 1, 17(2H, m) | $C_{15}H_{13}BrF_2N_2O_3$ 387, 19 | 46, 53 — | 3, 38 — Calculé F % 9, 81 | 7, 24 — | 20, 64 — |
| 42 | CDCl3 - 16, 75(1H, s); 7, 75(2H, d); 7, 37(2H, d); 3, 39(3H, s); 2, 10(1H, m); 1, 18(4H, m) | $C_{15}H_{13}N_3O_2$ 267, 29 | 67, 41 — | 4, 90 — | 15, 72 — | — — |
| 43 | CDCl3 - 16, 69(1H, s); 8, 33(2H, d); 7, 45(2H, d); 3, 42(3H, s); 2, 10(1H, pentet); 1, 18(4H, m) | $C_{14}H_{13}N_3O_4$ 287, 28 | 58, 53 — | 4, 56 — | 14, 63 — | — — |
| 44 | CDCl3 - 15, 70(1H, s); 7, 48(1H, s); 7, 33(4H, m); 2, 32(3H, s); 8, 12(3H, s); 1, 31(2H, m); 1, 17(2H, m) | $C_{15}H_{13}F_3N_2O_3$ 326, 28 | 55, 22 — | 4, 02 — | 8, 59 — | 17, 47 — |
| 45 | CDCl3 - 15, 62(1H, s); 7, 62(1H, s); 7, 46(3H, m); 2, 49(3H, t, J=3Hz); 2, 13(1H, m); 1, 34(2H, m); 1, 19(2H, m) | $C_{16}H_{13}F_5N_2O_2$ 360, 29 | 53, 34 — | 3, 64 — | 7, 78 — | 26, 37 — |
| 46 | CDCl3 - 17, 16(1H, s); 7, 60(1H, d); 7, 13(1H, d); 6, 96(1H, dd); 3, 30(3H, s); 2, 44(3H, s); 2, 13(1H, pentet); 1, 13(4H, m) | $C_{15}H_{15}BrN_2O_2$ 335, 21 | 53, 75 — | 4, 51 — | 8, 36 — | 23, 84 — |
| 47 | CDCl3 - 16, 82(1H, s, OH); 7, 57(1H, s, —NH); 7, 31-7, 26(3H, m, aromatic; 2, 75(2H, q, J=6Hz, ethyle —CH2); 2, 18-2, 08(1H, m, cyclopropyl 1-H); 1, 36-1, 10(4H, m, cyclopropyl); 1, 24 (3H, t, J=7, 6Hz, ethyl —CH3) | $C_{15}H_{15}ClN_2O_2$ 290, 75 | 61, 97 — | 5, 20 — | 9, 63 — | 12 ,19 — |
| 48 | | $C_{14}H_{12}N_2O_4$ 272, 26 | 61 ,76 — | 4, 44 — | 10, 29 — | — — |

EXAMPLE 50

Tablets were prepared containing 20 mg of the product of Example 1 or 2 and sufficient excipient of talc, lactose, starch and magnesium stearate for a final weight of 150 mg.

PHARMACEOLOGICAL DATA

A. The edema in the paw of the rat induced by carragenine was the test used. One hour after oral administration of the test compound or a control vehicle to groups of 6 to 12 male CFHB rats weighing 160 to 180 g, the rats received an injection of 1 mg of carragenine dissolved in 0.2 ml of saline solution in the heel of the right paw. The contralateral paw received control injections of the saline solution and the edema reactions in the paws was evaluated three hours later.

B. Edema to Hypersensibility of the retard type in the paw of DTH-M mice was the test used. Groups of 8 to 10 male CD-1 mice weighing 25 to 30 g were sensibilized by a subcutaneous injection of 1 mg of methyl bovine serum albumin (MBSA) in a volume of 0.2 ml of a saline solution/emulsion of complete Freund adjuvant FCA). The negative control group received injections of the saline solution/FCA emulsion and the DHT reactions of edema in the paw were evaluated 24 hours after defiance in the heel of the right paw with 0.1 mg of MBSA in a volume of 0.05 ml of saline solution on the seventh day after sensibilization. The contralateral paw received control injections of the saline solution. The test compounds or control vehicles were orally administered once a day on the 4th, 5th and 6th day and twice on the 7th day, one hour before and 6 hours after defiance of MBSA.

C. Edema to hypersensibility of the retard types of the paw of DTH-R rats were used. Groups of 8 to 12 male CFHB rats weighing 160 to 180 g were sensibilized with a subcutaneous injection to the base of the tail with a volume of 0.1 ml of FCA. The negative control groups received an injection of adjuvant free of FCA and the DTH reactions to edema of the paw were evaluated 24 hours after defiance of the heel of the right paw with 0.4 mg of an antigen extracts of Mycobacterium tuberculosis in a volume of 0.2 ml of saline solution on the 7th day after sensibilization. The contralateral paws received control injections of saline solutions. The test compounds were orally administered once a day on the 4th, 5th and 6th day and twice on the 7th day, 1 hour before and 6 hours after the antigen defiance. The test results are reported in Table II and the oral dosages are in unita of mg/kg.

TABLE II

| Example | Test 1 % inhibition | Dose | Test 2 % inhibition | Dose | Test 3 % inhibition | Dose |
| --- | --- | --- | --- | --- | --- | --- |
| 1 | 17 | (50) | 85 | (30) | 53 | (10) |
| 2 | 63 | (50) | 55 | (100) | 25 | (50) |
| 3 | 43 | (50) | 4 | (100) | −1 | (50) |
| 4 | 31 | (50) | 58 | (100) | 19 | (50) |
| 5 | 44 | (50) | 79 | (30) | 46 | (10) |
| 6 | 12 | (50) | 76 | (30) | 74 | (3) |
| 7 | 32 | (50) | 64 | (30) | 61 | (3) |
| 8 | 17 | (50) | 69 | (30) | 53 | (3) |
| 9 | 39 | (50) | 85 | (30) | 104 | (3) |
| 10 | 32 | (50) | 64 | (30) | 30 | (10) |
| 11 | 35 | (50) | 86 | (100) | 66 | (50) |
| 12 | 48 | (50) | 47 | (30) | 39 | (10) |
| 13 | 31 | (50) | 79 | (100) | 22 | (10) |
| 14 | −26 | (50) | 74 | (100) | 49 | (10) |
| 15 | 34 | (50) | 54 | (30) | 67 | (50) |
| 16 | 46 | (50) | 87 | (30) | 68 | (10) |
| 18 | 26 | (50) | 73 | (30) | 47 | (10) |
| 19 | 24 | (50) | 37 | (30) | 64 | (50) |
| 20 | 31 | (50) | 41 | (30) | 42 | (10) |
| 25 | 38 | (50) | 81 | (30) | 59 | (10) |
| 26 | −4 | (50) | 58 | (100) | 30 | (10) |
| 27 | 32 | (50) | 62 | (30) | 41 | (10) |
| 28 | 2 | (50) | 66 | (30) | 50 | (10) |
| 30 | 8 | (50) | 47 | (10) | 23 | (30) |
| 33 | 7 | (50) | 90 | (3) | 39 | (30) |

Various modifications of the compounds and methods of the invention may be made without departing from the spirit or scope thereof and it is to be understood that the invention is intended to be limited only as defined in the appended claims.

What is claimed is:

1. A compound of the formula

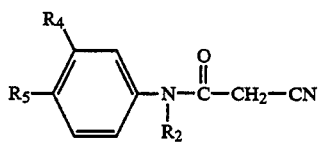

(IV)

wherein $R_5$ is —$CF_3$, $R_2$ is hydrogen or methyl and $R_4$ is methyl.

* * * * *

UNITED STATES PATENT AND TRADEMARK OFFICE
CERTIFICATE OF CORRECTION

PATENT NO. : 5,384,423

DATED : January 24, 1995

INVENTOR(S) : HAMBLETON et al

It is certified that error appears in the above-identified patent and that said Letters Patent is hereby corrected as shown below: Title page, In the Abstract, line 4 and in Column 1, line 30, change the structural formula to read

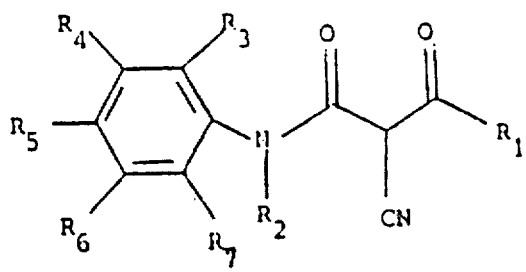

Signed and Sealed this

Twenty-second Day of August, 1995

Attest:

BRUCE LEHMAN

Attesting Officer     Commissioner of Patents and Trademarks